(12) United States Patent
Pommier et al.

(10) Patent No.: US 8,912,214 B2
(45) Date of Patent: Dec. 16, 2014

(54) USE OF CHK2 KINASE INHIBITORS FOR CANCER TREATMENT

(75) Inventors: Yves Pommier, Bethesda, MD (US); Robert H. Shoemaker, Boyds, MD (US); Dominic Scudiero, Frederick, MD (US); Michael Currens, Frederick, MD (US); John Cardellina, Walkersville, MD (US); Andrew Jobson, Rockville, MD (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 1777 days.

(21) Appl. No.: 11/989,737

(22) PCT Filed: Jul. 27, 2006

(86) PCT No.: PCT/US2006/029401
§ 371 (c)(1),
(2), (4) Date: Sep. 3, 2009

(87) PCT Pub. No.: WO2007/016338
PCT Pub. Date: Feb. 8, 2007

(65) Prior Publication Data
US 2010/0069423 A1    Mar. 18, 2010

Related U.S. Application Data

(60) Provisional application No. 60/703,556, filed on Jul. 29, 2005.

(51) Int. Cl.
| | | |
|---|---|---|
| *A61K 31/437* | (2006.01) | |
| *A61K 31/15* | (2006.01) | |
| *A61K 31/17* | (2006.01) | |
| *A61P 35/00* | (2006.01) | |
| *C07C 275/28* | (2006.01) | |
| *A61K 31/4184* | (2006.01) | |
| *C07C 281/16* | (2006.01) | |
| *C07C 251/44* | (2006.01) | |
| *A61K 31/175* | (2006.01) | |

(52) U.S. Cl.
CPC ............. *A61K 31/17* (2013.01); *A61K 31/4184* (2013.01); *C07C 2103/18* (2013.01); *C07C 281/16* (2013.01); *C07C 251/44* (2013.01); *A61K 31/175* (2013.01)
USPC ........... 514/286; 514/597; 514/632; 514/640; 514/19.3; 564/265; 564/51

(58) Field of Classification Search
CPC . A61K 31/17; A61K 31/175; A61K 31/4184; C07C 2103/18; C07C 251/44; C07C 281/16; G01N 33/574
USPC ............ 564/228, 265, 51; 514/632, 286, 597, 514/640, 19.3
See application file for complete search history.

(56) References Cited

U.S. PATENT DOCUMENTS

| | | |
|---|---|---|
| 3,560,566 A | 2/1971 | Marxer et al. |
| 4,369,172 A | 1/1983 | Schor et al. |
| 4,842,866 A | 6/1989 | Horder et al. |
| 5,217,720 A | 6/1993 | Sekigawa et al. |
| 6,569,457 B2 | 5/2003 | Ullah et al. |
| 6,638,534 B1 | 10/2003 | Ishibashi et al. |
| 2004/0214857 A1 | 10/2004 | Ameriks et al. |

FOREIGN PATENT DOCUMENTS

| | | |
|---|---|---|
| WO | 03006426 A1 | 1/2003 |
| WO | 2008156573 A1 | 12/2008 |

OTHER PUBLICATIONS

Antoni et al. (Nature Reviews Cancer, vol. 7, Dec. 2007 pp. 925-936.*
Sams-Dodd (Drug discovery today, vol. 10, No. 2, 2005, pp. 139-147.*
Horig et al. Journal of Translational Medicine 2004, 2(44) pp. 1-8.*
Schafer et al. Drug Discovery Today 2008, 13 (21/22), 913-916.*
Enrico Mihich, "Combined effects of chemotherapy and immunity against leukemia L1210 in DBA-2 mice," Cancer Research, 29: 848-854 (1969).
Korytnyk, et al., "Guanylhydrazones with potential antileukemic activity. 2. Synthesis and structure-activity relationships of analogs of 4,4'-diacetyl-N,N'-diphenylurea bis (guanylhydrazone)," Journal of Medicinal Chemistry, 21(6): 507-513 (1978).
Lowe, et al., "Intrinsic tumour suppression," Nature, 432: 307-315 (2004).
Marxer A. "A New Bis-Guanylhydrazone with Antileukemic Properties". Experientia, Mar. 15, 1967; 23(3) pp. 173-174.
International Preliminary Report on Patentability of the International Searching Authority; International Application No. PCT/US2006/029401; International Filing Date: Jul. 27, 2006; 9 Pages.
Written Opinion of the International Searching Authority; International Application No. PCT/US2006/029401; International Filing Date: Jul. 27, 2006; 8 Pages.
International Search Report of the International Searching Authority; International Application No. PCT/US2006/029401, International Filing Date: Jul. 27, 2006; Date of Mailing Mar. 12, 2007, 6 Pages.

* cited by examiner

*Primary Examiner* — Savitha Rao
(74) *Attorney, Agent, or Firm* — Cantor Colburn LLP

(57) ABSTRACT

Described herein are Chk2-inhibitor compounds and derivatives thereof, and methods of treating or preventing disease and disease symptoms using the compounds and compositions thereof.

20 Claims, 6 Drawing Sheets

Effect of NSC 109555 on Chk1 activity using the IMAP assay. 3 separate experiments are shown for NSC 109555. Staurosporine is shown as a positive control.

Effect of NSC 109555 on Chk2 activity using the IMAP assay. 3 separate experiments are shown for NSC 109555. Staurosporine is shown as a positive control.

Inhibition of Chk2 kinase activity by staurosporine using the *in vitro* Chk2 kinase assay. Top bands indicate level of Chk2 autophosphorylation, bottom bands indicate level of Histone H1 phosphorylation

NSC 109555

Chk2

Inhibition of Chk2 kinase activity by NSC 109555 using the *in vitro* kinase assay. Top bands indicate level of Chk2 autophosphorylation, bottom bands indicate level of Histone H1 phosphorylation

Chk1

Inhibition of Chk1 kinase activity by NSC 109555 using the *in vitro* kinase assay. Top bands indicate level of Chk1 autophosphorylation, bottom bands indicate level of Histone H1 phosphorylation

USE OF CHK2 KINASE INHIBITORS FOR CANCER TREATMENT

STATEMENT REGARDING FEDERALLY SPONSORED RESEARCH OR DEVELOPMENT

Research supporting this application was carried out by the United States of America as represented by the Secretary, Department of Health and Human Services.

The present application claims priority of U.S. provisional application No. 60/703,556 filed Jul. 29, 2006, which is incorporated by reference herein in its entirety.

BACKGROUND OF THE INVENTION

Tumorigenesis is an evolutionary process that selects for genetic and epigenetic changes, allowing evasion of antiproliferative and cell death inducing mechanisms that normally limit clonal expansion of somatic cells. Lowe et al., Nature, 432, 307-315 (2004).

It has been hypothesized that DNA damage checkpoints might become activated in the early stages of tumorigenesis, leading to cell-cycle blockade or apoptosis, either of which might constrain tumor progression. The ATM-Chk2 kinase pathway has been implicated in this process. As such, members of that pathway, including Chk2, are thought to play a role in tumorigenesis. Thus, modulators of members of the ATM-Chk2 pathway may be implicated as anticancer agents, and their use, either alone or in combination with other anticancer agents, may provide new strategies for treatment or prevention of cancer, and other diseases, disorders, and symptoms thereof where apoptotic cell death is associated.

SUMMARY OF THE INVENTION

Described herein are compounds, and compositions and methods of generating the compounds thereof, methods of treating disease and disease symptoms, and compounds useful for modulating biological processes for treating disease and disease symptoms.

One embodiment is a compound of formula (I), (II), or (III) or pharmaceutically acceptable salt, solvate or hydrate thereof:

Formula (I)
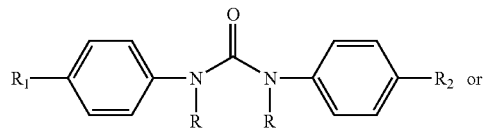

Formula (II)
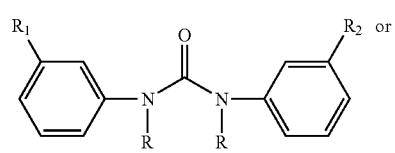

Formula (III)
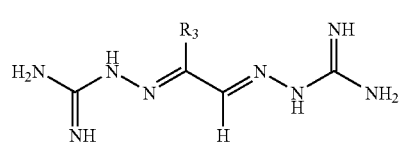

wherein,
each $R_1$ and $R_2$ is independently is

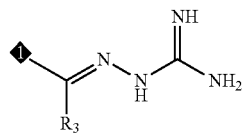

each $R_3$ is independently alkyl; and
each R is independently H or alkyl.

In other embodiments, the compounds are those of Formula (I), (II) or (III) or other formulae herein:
wherein each R is independently H;
wherein each R is independently alkyl;
wherein each $R_3$ is independently C1-C6alkyl;
wherein each R is independently alkyl and each $R_3$ is methyl;
wherein each R is independently alkyl and each $R_3$ is ethyl;
wherein each R is independently alkyl and each $R_3$ is propyl;
wherein each R is independently alkyl and each $R_3$ is butyl;
wherein each R is independently H and each $R_3$ is methyl;
wherein each R is independently H and each $R_3$ is ethyl;
wherein each R is independently H and each $R_3$ is propyl;
wherein each R is independently H and each $R_3$ is butyl;
wherein each R is independently H and one $R_3$ is ethyl and the other $R_3$ is methyl;
wherein each R is independently H and one $R_3$ is propyl and the other $R_3$ is methyl;
wherein each R is independently H and one $R_3$ is propyl and the other $R_3$ is ethyl;
wherein one R is independently alkyl and the other R is independently H;
wherein each R is independently allyl.

Another aspect is a compound of formula (IV) or (V), or pharmaceutically acceptable salt, solvate or hydrate thereof:

Formula (IV)
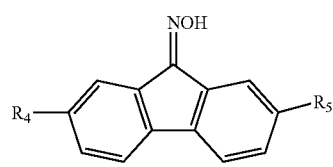

wherein,
each $R_4$ and $R_5$ is independently C(Me)=N(OH), $NO_2$, or H;

Formula (V)
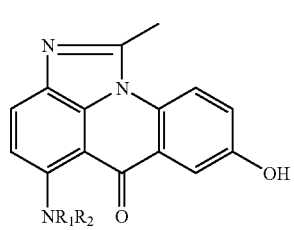

wherein, $R_1$ is independently H, or alkyl optionally substituted with $NR_6R_7$;

$R_2$ is independently H, or alkyl optionally substituted with $NR_6R_7$;

each $R_6$ is independently H or alkyl; and each $R_7$ is independently H or alkyl.

Other aspects of compounds of Formula (IV) include those:

wherein one of $R_4$ and $R_5$ is independently C(Me)=N(OH);
wherein one of $R_4$ and $R_5$ is independently H;
wherein $R_4$ and $R_5$ are the same; and
wherein $R_4$ and $R_5$ are different.

Other aspects of compounds of Formula (V) include those:
wherein $R_1$ is independently H, and $R_2$ is alkyl optionally substituted with $NR_6R_7$;
wherein each of $R_1$ and $R_2$ is independently alkyl optionally substituted with $NR_6R_7$;
wherein one of $R_6$ and $R_7$ are each independently alkyl;
wherein one of $R_6$ and $R_7$ is H and the other is alkyl;
wherein $R_6$ and $R_7$ are the same; and
wherein $R_6$ and $R_7$ are different.

Another aspect is a composition including a compound of any of the formulae herein and a pharmaceutically acceptable carrier. The composition can also include an additional therapeutic agent (e.g., anticancer agents). Additional anticancer agents include, for example, an antiangiogenesis agent, selective estrogen-receptor modulator (SERM), breast cancer therapeutic agent, aromatase inhibitor, biologic response modifiers, hormonal therapies agent, anthracycline, taxane, alkylating agent, taxol, cisplatin, arabinofuranosyl cytosine (ara-C), 5-fluorouracil (5-FU), altretamine, busulfan, chlorambucil, cyclophosphamide, ifosfamide, mechlorethamine, melphalan, thiotepa, cladribine, fluorouracil, floxuridine, gemcitabine, thioguanine, pentostatin, methotrexate, 6-mercaptopurine, cytarabine, carmustine, lomustine, streptozotocin, carboplatin, oxaliplatin, iproplatin, tetraplatin, lobaplatin, JM216, JM335, fludarabine, aminoglutethimide, flutamide, goserelin, leuprolide, megestrol acetate, cyproterone acetate, tamoxifen, anastrozole, bicalutamide, dexamethasone, diethylstilbestrol, prednisone, bleomycin, dactinomycin, daunorubicin, doxirubicin, idarubicin, mitoxantrone, losoxantrone, mitomycin-c, plicamycin, paclitaxel, docetaxel, CPI-11, epothilones, topotecan, irinotecan, 9-amino camptothecan, 9-nitro camptothecan, GS-211, etoposide, teniposide, vinblastine, vincristine, vinorelbine, procarbazine, asparaginase, pegaspargase, methoxtrexate, octreotide, estramustine, hydroxyurea, tamoxifen, raloxifene, toremifene, exemestane, letrozole, anastrozole, megestrol, trastuzumab, goserelin acetate, fulvestrant, doxorubicin, epirubicin, or cyclophosphonamide and the like.

One aspect is a method of treating a subject suffering from or susceptible to a disease or disorder, or symptom thereof, or preventing a disease or disorder, or symptom thereof, in a subject susceptible to a disease or disorder, or symptom thereof, or reducing the risk of development in a subject of a disease or disorder, or symptom thereof. The method includes the step of administering to the subject a therapeutic amount of a compound herein sufficient to treat the disease or disorder or symptom thereof under conditions such that the disease or disorder or symptom thereof is treated. In certain embodiments, the disease or disorder is a cancer or proliferative disease or disorder. In certain embodiments, the subject is a human. In certain embodiments, the subject is identified as being in need of such treatment. In certain embodiments, the subject is not suffering from a cancer. In certain embodiments, the subject is "at risk" of developing cancer. In certain embodiments, the method includes administration of an additional therapeutic agent. In certain embodiments, the step of administering comprises administering the compound orally, intravenously or intramuscularly.

The methods of the invention also may include the step of identifying that the subject is in need of treatment of diseases or disorders described herein, e.g., identifying that the subject is in need of Chk2 inhibitor administration; or in need of treatment of cancer including (e.g. cancer of colon, lung, breast, bladder, melanoma, prostate or other solid malignancies); or in need of treatment of hypoxia, diabetes, stroke, or an auto-immune disease; or in need of modulated Chk2 phosphorylation; or in need of protecting non-cancerous tissue e.g. from occurrence of cancer cells; or in need of reducing apoptotis in cancerous cells; or in need of sensitizing a cancer cell (e.g. mammalian cancer cells particularly human cancer cells) to one or more anticancer agents. The identification can be in the judgment of a subject or a health professional and can be subjective (e.g., opinion) or objective (e.g., measurable by a test or a diagnostic method). Tests for identification are disclosed herein and may include e.g. biopsy or other diagnosis. Thus, in such methods, a sample of biological material, such as blood, plasma, semen, saliva, extracted cells or tissue, etc., may be obtained from the subject to be tested. Thus, the methods of the invention can include the step of obtaining a sample of biological material (such as a bodily fluid, cells or tissue) from a subject; testing the sample to determine the presence or absence of a condition such as the presence of absence of cancer cells, or other marker; and determining whether the subject is in need of treatment according to the invention.

More particularly, in certain embodiments, methods of the invention may further include the step of determining a level of a marker (Marker) in the subject. In certain embodiments, the step of determining of the level of Marker is performed prior to administration of the compound of the formulae herein to the subject. In certain embodiments, the determining of the level of Marker is performed subsequent to administration of the compound of the formulae herein to the subject. In certain embodiments, the determining of the level of Marker is performed prior to and subsequent to administration of the compound of the formulae herein to the subject. In certain embodiments, the levels of Marker performed prior to and subsequent to administration of the compound of the formulae herein to the subject are compared. In certain embodiments, the comparison of Marker levels is reported by a clinic, laboratory, or hospital agent to a health care professional. In certain embodiments, when the level of Marker performed prior to administration of the compound of the formulae herein to the subject is lower or higher (depending on the Marker) than the level of Marker performed subsequent to administration of the compound of the formulae herein to the subject, then the amount of compound administered to the subject is an effective amount. The Marker can be any characteristic or identifier, including for example, a chemical, a fluid, a protein, gene, promoter, enzyme, protein, labeled molecule, tagged molecule, antibody, and the like (e.g., Marker; Chk2, phosphorylation of a kinase, p53, E2F1, PML, Cd25 phosphatases, Brcal).

Another aspect is a method of protecting normal (e.g., non-cancerous tissue) in a subject, the method comprising the steps of identifying a subject as in need thereof and administering to the subject a therapeutic amount of a compound of the formulae herein sufficient to protect normal tissue.

Another aspect is a method of reducing apoptosis in a normal cell (e.g., non-cancerous cell) in a subject, the method comprising the steps of identifying a subject as in need thereof and administering to the subject a therapeutic amount of a compound of the formulae herein sufficient to reduce apoptosis in a normal cell.

Another aspect is a method of modulating a substrate (e.g., p53, E2F1, PML) in a normal cell (e.g., non-cancerous cell) in a subject, the method comprising the steps of identifying a subject as in need thereof and administering to the subject a therapeutic amount of a compound of the formulae herein sufficient to modulate the substrate in a normal cell.

Another aspect is a method of treating or preventing hypoxia, diabetes, strokes, or auto-immune disease in a subject, the method comprising the steps of identifying a subject as in need thereof and administering to the subject a therapeutic amount of a compound of the formulae herein sufficient to reduce apoptosis in a normal cell.

Another aspect is a method of sensitizing a cancer cell in a subject to an anticancer agent or DNA targeted agent (e.g., chemotherapeutic), the method comprising the steps of identifying a subject as in need thereof and administering to the subject a therapeutic amount of a compound of the formulae herein sufficient to sensitizing a cancer cell in a subject to an anticancer agent or DNA targeted agent.

Another aspect is a method of treating or preventing cancer in a subject, the method comprising the steps of and administering to the subject a therapeutic amount of a compound of the formulae herein. In another aspect, the method further comprises administration of an additional anticancer agent. In another aspect, the additional anticancer agent is a DNA targeted agent (e.g., chemotherapeutic).

In other aspects, the cancer is colon, lung, breast, bladder, melanoma, prostate or other solid malignancies.

In another aspect, the method further comprises administration of radiation including ionizing radiation in conjunction with administration compounds of any one of formula (I), (II), (III), (IV), (V) or other formulae herein.

In such aspects, in certain methods of treating a patient suffering from or susceptible to cancer, the dose of ionizing radiation administered to the cell is between about 0.01 Gy to about 100 Gy, between about 0.5 Gy to about 50 Gy, or between about 1 Gy to about 20 Gy for each dose.

In certain other methods of treating a patient suffering from or susceptible to cancer, the patient is administered a protocol in which a compound of any one of formula (I), (II), (III), (IV), or (V), or other formulae herein and ionizing radiation are co-administered two or more times. Thus, in certain methods, the patient is administered with between about 2 and about 50 doses of a compound of any one of formula (I), (II), (III), (N), or (V), or other formulae herein and ionizing radiation. Suitable protocols may comprise administering the a compound of formula I and ionizing radiation to the patient 2 to 7 times per week for between 2 and about 10 weeks, 3 to 6 times between 3 and about 8 weeks, or 4 to 5 times between about 4 and about 7 weeks. In other methods, the protocol comprises administering a compound of any one of formula (I), (II), (III), (IV), or (V), or other formulae herein and ionizing radiation to the patient 4, 5 or 6 times per week for between 3 and about 7 weeks, or more preferably between 4 and about 6 weeks. The individual dose of ionizing radiation administered to the patient is suitably between about 0.5 Gy and about 4 Gy per dose (or between about 1 Gy and about 3 Gy per dose) such that the aggregate amount of radiation administered to the patient is between about 40 Gy and about 120 Gy, between about 55 Gy and about 90 Gy.

It is understood that in such methods the order of administration of a compound of any one of formula (I), (II), (III), (IV) or (V) or other formulae herein and ionizing radiation to the patient, can be sequential or contemporaneous.

Thus, in certain methods the cells or patients are administered a compound of any one of formula (I), (II), (III), (IV) or (V) or other formulae herein prior to administering the ionizing radiation. In certain other methods a compound any one of formula (I), (II), (III), (IV) or (V) or other formulae herein is contacted with the cells after administering the ionizing radiation. In yet other methods, the step of contacting of a compound of any one of formula (I), (II), (III), (IV) or (V) or other formulae herein with the cells and the step of administering the ionizing radiation to the cells occur contemporaneously. In methods in which a compound of any one of formula (I), (II), (IV) or (V) or other formulae herein and ionizing radiation are administered sequentially, the time period separating administration of the drug and the radiation is typically between about 15 minutes and about 48 hours, between about 15 minutes and 24 hours, or between 1 hour and 18 hours. In certain methods comprising sequential addition of a compound of any of any one of formula (I), (II), (III), (IV) or (V) or other formulae herein and ionizing radiation, the delay period between administration of the drug and radiation is about 1 hour, 2 hours, 3 hours, 4 hours, 6 hours, 8 hours, 12 hours, or 16 hours.

In certain methods of treating a patient suffering from or susceptible to cancer, it is preferable to limit the patient's exposure to ionizing radiation to that portion of the body in which the cancer or tumor is located. Thus, ionizing radiation sources which can be locally administered are generally preferred. Certain ionizing radiation sources include X-Ray sources, other high energy light sources (including gamma-ray sources and certain high energy UV light sources) and injectable radiotherapeutic agents comprising one or more radioisotopes that emit one or more high energy particles capable of double strand DNA cleavage. Preferred radiometal ions include isotopes of metal ions that emit $\alpha$, $\beta^-$, $\beta^+$ or $\gamma$ radiation, including technetium, rhenium, yttrium, copper, gallium, indium, bismuth, platinum rhodium and iodine radioisotopes. In certain methods of the invention, X-ray irradiation is a preferred method of administering ionizing radiation to a patient.

Another aspect is a method of modulating a protein (e.g., Cdc25 phosphatases, Brcal) in a subject, the method comprising the steps of identifying a subject as in need thereof and administering to the subject a therapeutic amount of a compound of the formulae herein sufficient to modulate the protein (e.g., Cdc25 phosphatases, Brcal).

Another aspect is a method of modulating Chk2 phosphorylation in a subject, the method comprising the steps of identifying a subject as in need thereof and administering to the subject a therapeutic amount of a compound of any of the formulae herein sufficient to modulate Chk2 phosphorylation under conditions such that the Chk2 phosphorylation is modulated. In one aspect, the modulation is down regulation.

In one embodiment, the compounds delineated herein are selective for Chk2 v. Chk1. Selective (or selectivity) refers to inhibition of Chk2 relative to Chk1 by N-times greater, where N is an integer between 2 and 25 inclusive (e.g., >2x, >3x, >4x, >5x, >10x, >20x, >25x).

A method of treating or preventing a subject suffering from or susceptible to a disease or disorder, the method comprising the steps of (i) identifying the patient as one who may benefit from, or is in need of, Chk2 inhibition; and (ii) administering to the subject a therapeutic amount of a compound of the formulae herein sufficient to treat or prevent the disease or disorder or symptoms thereof under conditions such that the disease or disorder is treated or prevented.

In another aspect, an embodiment provides kits for treatment of a disease(s) or disorder(s) or symptoms thereof, including those of a proliferative disorder nature. In one embodiment, the kit includes an effective amount of a compound of the formulae herein in unit dosage form, together with instructions for administering the compound of the formulae hereinto a subject suffering from or susceptible to a disease or disorder or symptoms thereof, including those of a proliferative disorder nature. In preferred embodiments, the compound of the formulae herein is any of the specific compounds delineated herein.

Another aspect is a method of modulating a target, including a cell cycle checkpoint protein, programmed cell death substrate, or a kinase identified herein, in a cell comprising contacting a compound of any of the formulae herein with a target (e.g., in a subject, in a cell, in vitro) such that the target is modulated. The method can also include modulating the target in a subject by administering the compound to the subject.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

Another aspect is a method of making a pharmaceutical composition delineated herein, including the step of combining a compound herein (e.g., a compound of any of the formulae herein) with a pharmaceutically acceptable carrier. The method can further include combining an additional therapeutic agent with the compound and/or carrier.

Table A lists compounds (or salts or solvates thereof) that are representative embodiments of the formulae herein and are useful in the methods delineated herein.

TABLE A

Compounds

TABLE A-continued

Compounds

7

[Chemical structure: 2,7-dinitro-9H-fluoren-9-one oxime]

8

[Chemical structure: imidazo-fused tricyclic compound with CH3, NH, OH, and diethylaminopropyl substituents]

DETAILED DESCRIPTION OF THE INVENTION

I. Diseases, Disorders and Symptoms Thereof

Figure 1:
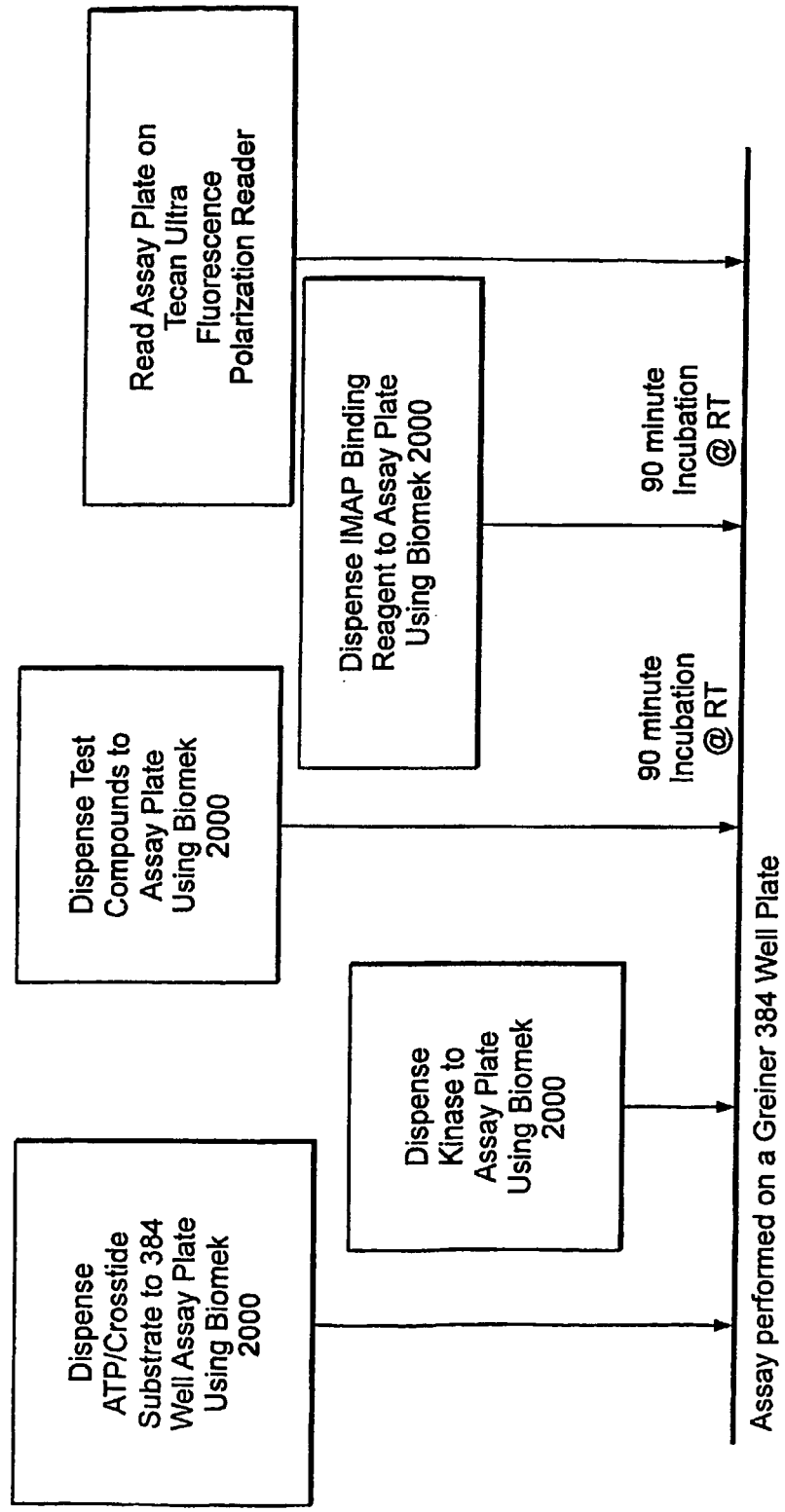
FIG. 1 illustrates Principles of the IMAP Chk2 Assay System.

As noted, diseases, disorders or symptoms thereof of specific interest include cancer, those wherein proliferation may be implicated. Specifically, cancers or proliferative disorders include breast, prostate, lung, colon, liver, solid tumor, myeloma, leukemia, bladder, stomach, and the like; diseases, disorders or symptoms thereof involving inhibition of Chk2, or diseases, disorders or symptoms thereof wherein targets and/or substrates associated with the diseases, disorders or symptoms thereof are mediated by Chk2.

II. Compounds

Another aspect is a radiolabeled compound of any of the formulae delineated herein. Such compounds have one or more radioactive atoms or heavy atom isotopes (e.g., $^3H$, $^2H$, $^{14}C$, $^{13}C$, $^{35}S$, $^{125}I$, $^{131}I$) introduced into the compound. Such compounds are useful for drug metabolism studies and diagnostics.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl substituent group. The term "ester" refers to a —C(O)O—R, wherein R is as defined herein. An "amido" is an —C(O)NH$_2$, and an "N-alkyl-substituted amido" is of the formula C(O)NHR, wherein R is as defined herein.

The term "mercapto" refers to a —SH group.

As used herein, the term "halogen" or "halo" means —F, —Cl, —Br or —I.

As used herein, the term "haloalkyl" means and alkyl group in which one or more (including all) the hydrogen radicals are replaced by a halo group, wherein each halo group is independently selected from F, —Cl, —Br, and —I. The term "halomethyl" means a methyl in which one to three hydrogen radical(s) have been replaced by a halo group. Representative haloalkyl groups include trifluoromethyl, difluoromethyl, bromomethyl, 1,2-dichloroethyl, 4-iodobutyl, 2-fluoropentyl, and the like. The term "perhaloalkyl" refers to a alkyl group in which all hydrogen atoms are replaced by a halo group (e.g., trifluoromethyl, pentafluoroethyl).

The term "cycloalkyl" refers to a hydrocarbon 3-10 membered monocyclic or 7-14 membered bicyclic ring system having at least one non-aromatic ring. Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclooctyl, cyclononyl, and cyclodecyl.

The term "cycloalkenyl" refers to a hydrocarbon 3-8 membered monocyclic or 7-14 membered bicyclic ring system having at least one non-aromatic ring, wherein the non-aromatic ring has some degree of unsaturation. Cycloalkenyl groups may be optionally substituted with one or more substituents. In one embodiment, 0, 1, 2, 3, or 4 atoms of each ring of a cycloalkenyl group may be substituted by a substituent. Examples of cycloalkenyl groups include cyclohexenyl, bicyclo[2.2.1]hept-2-enyl, dihydronaphthalenyl, benzocyclopentyl, cyclopentenyl, cyclopentadienyl, cyclohexenyl, cyclohexadienyl, cycloheptenyl, cycloheptadienyl, cycloheptatrienyl, cyclooctenyl, cyclooctadienyl, cyclooctatrienyl, cyclooctatetraenyl, cyclononenyl, cyclononadienyl, cyclodecenyl, cyclodecadienyl and the like.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

As used herein, the term "arylalkyl" means an aryl group that is attached to another group by a ($C_1$-$C_6$)alkylene group. Arylalkyl groups may be optionally substituted, either on the aryl portion of the arylalkyl group or on the alkylene portion of the arylalkyl group, with one or more substituent. Representative arylalkyl groups include benzyl, 2-phenyl-ethyl, naphth-3-yl-methyl and the like.

As used herein, the term "alkylene" refers to an alkyl group that has two points of attachment. The term "($C_1$-$C_6$)alkylene" refers to an alkylene group that has from one to six carbon atoms. Non-limiting examples of alkylene groups include methylene (—$CH_2$—), ethylene (—$CH_2CH_2$—), n-propylene (—$CH_2CH_2CH_2$—), isopropylene (—$CH_2CH(CH_3)$—), and the like.

The term "arylalkoxy" refers to an alkoxy substituted with aryl.

The term "heteroaryl" refers to an aromatic monocyclic, bicyclic, or tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, 1-oxo-pyridyl, furanyl, benzo[1,3]dioxolyl, benzo[1,4]dioxinyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, and benzo(b)thienyl, 3H-thiazolo[2,3-c][1,2,4]thiadiazolyl, imidazo[1,2-d]-1,2,4-thiadiazolyl, imidazo[2,1-b]-1,3,4-thiadiazolyl, 1H,2H-furo[3,4-d]-1,2,3-thiadiazolyl, 1H-pyrazolo[5,1-c]-1,2,4-triazolyl, pyrrolo[3,4-d]-1,2,3-triazolyl, cyclopentatriazolyl, 3H-pyrrolo[3,4-c]isoxazolyl, 1H,3H-pyrrolo[1,2-c]oxazolyl, pyrrolo[2,1b]oxazolyl, and the like.

As used herein, the term "heteroarylalkyl" means a heteroaryl group that is attached to another group by a ($C_1$-$C_6$) alkane. Heteroarylalkyl groups may be optionally substituted, either on the heteroaryl portion of the heteroaralkyl group or on the alkyl portion of the heteroarylallyl group, with one or more substituents. Representative heteroaralkyl groups include 2-(pyridin-4-yl)-propyl, 2-(thien-3-yl)-ethyl, imidazol-4-yl-methyl and the like.

As used herein, the term "heteroarylalkenyl" means a heteroaryl group that is attached to another group by a ($C_1$-$C_6$) alkenyl. Heteroarylalkenyl groups may be optionally substituted, either on the heteroaryl portion of the heteroaralkenyl group or on the alkenyl portion of the heteroarylalkenyl group, with one or more substituents. Representative heteroaralkenyl groups include 2-(pyridin-4-yl)-propenyl, 2-(thien-3-yl)-ethenyl, imidazol-4-yl-butenyl and the like.

The term "heterocycloallyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si. Heterocycloallyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, 2-oxopiperazinyl, 2-oxopiperidinyl, 2-oxopyrrolidinyl, 4-piperidonyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane, tetrahydrofuranyl, tetrahydrothienyl, thiirene.

The term "heterocycloalkenyl" refers to a nonaromatic 5-8 membered monocyclic, 8-12 membered bicyclic, or 11-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system has some degree of unsaturation. Heterocycloalkenylyl groups may be optionally substituted with one or more substituents. In one embodiment, 0, 1, 2, 3, or 4 atoms of each ring of a heterocycloalkenylyl group may be substituted by a substituent. Examples of these groups include 2-pyrrolinyl, 3-pyrrolinyl, 4H-pyranyl, 2-pyrazolinyl, dihydrofuranyl, dihydrothiophenyl, 2-imidazolinyl, indolinyl and the like.

The term "alkylamino" refers to an amino substituent which is further substituted with one or two alkyl groups. The term "aminoalkyl" refers to an alkyl substituent which is further substituted with one or more amino groups. The term "mercaptoalkyl" refers to an alkyl substituent which is further substituted with one or more mercapto groups. The term "hydroxyalkyl" refers to an alkyl substituent which is further substituted with one or more hydroxy groups. The term "sulfonylalkyl" refers to an alkyl substituent which is further substituted with one or more sulfonyl groups. The term "sulfonylaryl" refers to an aryl substituent which is further substituted with one or more sulfonyl groups. The term alkylcarbonyl refers to an —C(O)-alkyl. The term "mercaptoalkoxy" refers to an alkoxy substituent which is further substituted with one or more mercapto groups.

The term "alkylcarbonylalkyl" refers to an alkyl substituent which is further substituted with —C(O)-alkyl. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

As used herein the term "substituent" or "substituted" means that a hydrogen radical on a compound or group (such as, for example, alkyl, alkenyl, alkynyl, alkylene, aryl, arylalkyl, heteroaryl, heteroarylalkyl, cycloalkyl, cycloalkenyl, heterocycloalkyl, or heterocycloalkylalkyl group) is replaced with any desired group that does not substantially adversely affect the stability of the compound. In one embodiment, desired substituents are those which do not adversely affect the activity of a compound. The term "substituted" refers to one or more substituents (which may be the same or different), each replacing a hydrogen atom. Examples of substituents include, but are not limited to, halogen (F, Cl, Br, or I), hydroxyl, amino, alkylamino, arylamino, dialkylamino, diarylamino, cyano, nitro, mercapto, oxo (i.e., carbonyl), thio, imino, formyl, carbamido, carbamyl, carboxyl, thioureido, thiocyanato, sulfoamido, sulfonylalkyl, sulfonylaryl, alkyl, alkenyl, alkoxy, mercaptoalkoxy, aryl, heteroaryl, cycloalkenyl, heterocycloalkyl, heterocycloalkenyl, wherein alkyl, alkenyl, alkyloxy, aryl, heteroaryl, cycloalkyl, cycloalkenyl, heterocycloalkyl, and heterocycloalkenyl are optionally substituted with alkyl, aryl, heteroaryl, halogen, hydroxyl, amino, mercapto, cyano, nitro, oxo (=O), thioxo (=S), or imino (=NR), wherein R is as defined herein.

In other embodiments, substituents on any group (such as, for example, alkyl, alkenyl, alkynyl, aryl, arylalkyl, heteroaryl, heteroarylalkyl, cycloalkyl, cycloalkenyl, heterocycloalkyl, and heterocycloalkenyl) can be at any atom of that group, wherein any group that can be substituted (such as, for example, alkyl, alkenyl, alkynyl, aryl, arylalkyl, heteroaryl, heteroarylalkyl, cycloalkyl, cycloalkenyl, heterocycloalkyl, and heterocycloalkenyl) can be optionally substituted with one or more substituents (which may be the same or different), each replacing a hydrogen atom. Examples of suitable substituents include, but not limited to alkyl, alkenyl, alkynyl, cycloalkyl, cycloalkenyl, heteroaryl, heterocycloalkenyl, heterocycloalkyl, arylalkyl, heteroarylalkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, or alkoxycarbonylamino; alkylamino, arylamino, diarylamino, alkylcarbonyl; or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Additional suitable substituents on alkyl, alkenyl, alkynyl, aryl, arylalkyl; heteroaryl, heteroarylalkyl, cycloalkyl, cycloalkylalkyl, cycloalkenyl, heterocycloalkyl, and heterocycloalkenyl include, without limitation halogen, CN, $NO_2$, $OR^{15}$, $SR^{15}$, $S(O)_2OR^{15}$, $NR^{15}R^{16}$, $C_1$-$C_2$ perfluoroalkyl, $C_1$-$C_2$ perfluoroalkoxy, 1,2-methylenedioxy, (=O), (=S), (=$NR^{15}$), $C(O)OR^{15}$, $C(O)NR^{15}R^{16}$, $OC(O)NR^{15}R^{16}$, $NR^{15}C(O)NR^{15}R^{16}$, $C(NR^{16})NR^{15}R^{16}$, $NR^{15}C(NR^{16})NR^{15}R^{16}$, $S(O)_2NR^{15}R^{16}$, $R^{17}$, $C(O)H$, $C(O)R^{17}$, $NR^{15}C(O)R^{17}$, $Si(R^{15})_3$, $OSi(R^{15})_3$, $Si(OH)_2R^{15}$, $P(O)(OR^{15})_2$, $S(O)R^{17}$, or $S(O)_2R^{17}$. Each $R^{15}$ is independently hydrogen, $C_1$-$C_6$ alkyl optionally substituted with cycloalkyl, aryl, heterocloalkyl, heterocycloalkenyl, or heteroaryl. Each $R^{16}$ is independently hydrogen, $C_3$-$C_6$ cycloalkyl, aryl, heterocycloalkyl, heterocycloalkenyl, heteroaryl, $C_1$-$C_4$ alkyl or $C_1$-$C_4$ alkyl substituted with $C_3$-$C_6$ cycloalkyl, aryl, heterocycloalkyl, heterocycloalkenyl, or heteroaryl. Each $R^{17}$ is independently $C_3$-$C_6$ cycloalkyl, aryl, heterocycloalkyl, heterocycloalkenyl, heteroaryl, $C_1$-$C_4$ allyl or $C_1$-$C_4$ alkyl substituted with $C_3$-$C_6$ cycloalkyl, aryl, heterocycloalkyl, heterocycloalkenyl, or heteroaryl. Each $C_3$-$C_6$ cycloalkyl, aryl, heterocycloalkyl, heterocycloalkenyl, heteroaryl and $C_1$-$C_4$ alkyl in each $R^{15}$, $R^{16}$ and $R^{17}$ can optionally be substituted with halogen, CN, $C_1$-$C_4$ alkyl, OH, $C_1$-$C_4$ alkoxy, COOH, $C(O)OC_1$-$C_4$ alkyl, $NH_2$, $C_1$-$C_4$ alkylamino, or $C_1$-$C_4$ dialkylamino.

As used herein, the term "lower" refers to a group having up to six atoms. For example, a "lower alkyl" refers to an alkyl radical having from 1 to 6 carbon atoms, and a "lower alkenyl" or "lower alkynyl" refers to an alkenyl or alkynyl radical having from 2 to 6 carbon atoms, respectively.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., formulation into therapeutic products, intermediates for use in production of therapeutic compounds, isolatable or storable intermediate compounds, treating diseases, disorders, or symptoms thereof, including those delineated herein). The compounds produced by the methods herein can be incorporated into compositions, including solutions, capsules, crèmes, or ointments for administration to a subject (e.g., human, animal). Such compositions (e.g., pharmaceuticals) are useful for providing to the subject desirable health or other physiological benefits that are associated with such compounds.

The compounds of the formulae herein are available from commercial sources or may be synthesized using reagents and techniques known in the art, including those delineated herein. The chemicals used in the synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the compounds herein. In addition, various synthetic steps may be performed in an alternate sequence or order to give the desired compounds. Synthetic chemistry transformations and protecting group methodologies (protection and deprotection) useful in synthesizing the applicable compounds are known in the art and include, for example, those described in R. Larock, *Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The compounds of this invention include the compounds themselves, as well as their salts, solvate, hydrate, polymorph, or prodrugs, if applicable. As used herein, the term "pharmaceutically acceptable salt," is a salt formed from, for example, an acid and a basic group of a compound of any one of the formulae disclosed herein. Illustrative salts include, but are not limited to, sulfate, citrate, acetate, chloride, bromide, iodide, nitrate, bisulfate, phosphate, acid phosphate, lactate, salicylate, acid citrate, tartrate, oleate, tannate, pantothenate, bitartrate, ascorbate, succinate, maleate, besylate, fumarate, gluconate, glucaronate, saccharate, formate, benzoate, glutamate, methanesulfonate, ethanesulfonate, benzenesulfonate, and p-toluenesulfonate salts. The term "pharmaceutically acceptable salt" also refers to a salt prepared from a compound of any one of the formulae disclosed herein having an acidic functional group, such as a carboxylic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of any one of the formulae disclosed herein having a basic functional group, such as an amino functional group, and a pharmaceutically acceptable inorganic or organic acid. Suitable acids include hydrogen sulfate, citric acid, acetic acid, hydrochloric acid (HCl), hydrogen bromide (HBr), hydrogen iodide (HI), nitric acid, phosphoric acid, lactic acid, salicylic acid, tartaric acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, and p-toluenesulfonic acid.

As used herein, the term "hydrate" means a compound of the present invention or a salt thereof, which further includes a stoichiometric or non-stoichiometric amount of water bound by non-covalent intermolecular forces.

In certain aspects, preferred compounds including for use in methods disclosed herein may include a compound of the following Formula (I), or pharmaceutically acceptable salt, solvate or hydrate thereof:

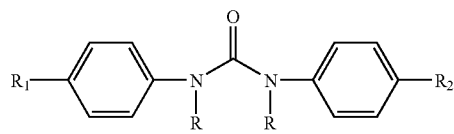

(I)

wherein each $R_1$ and $R_2$ is independently:

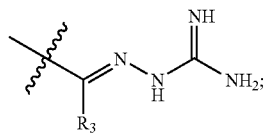

each $R_3$ is independently alkyl; and
each R is independently H or alkyl, wherein both R groups are not H.

In certain preferred compounds of Formula (I), suitably one R may be alkyl and the other R is independently H. Also preferred are compounds of formula (I) wherein each R is independently alkyl.

In certain aspects, preferred compounds including for use in methods disclosed herein may include a compound of the following Formula (II), or pharmaceutically acceptable salt, solvate or hydrate thereof:

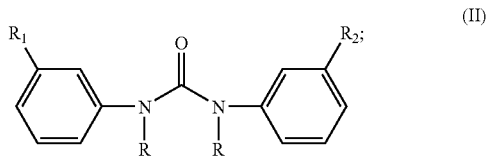

(II)

wherein each $R_1$ and $R_2$ is independently:

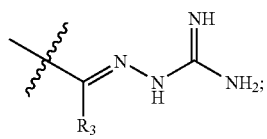

each $R_3$ is independently alkyl; and
each R is independently H or alkyl, wherein both R groups are not H.

In yet additional aspects, preferred compounds including for use in methods disclosed herein may include a compound of the following Formula (IV), or pharmaceutically acceptable salt, solvate or hydrate thereof:

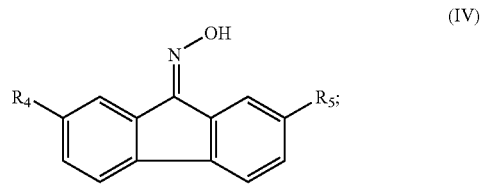

(IV)

wherein each $R_4$ and $R_5$ is independently C(Me)=N(OH), $NO_2$, or H;
wherein $R_4$ and $R_5$ are both not H.

Also preferred are pharmaceutical compositions that comprise (i) one or more compounds of the following Formulae (I), (II), or (IV) or pharmaceutically acceptable salt, solvate or hydrate thereof and (ii) a pharmaceutically acceptable carrier:

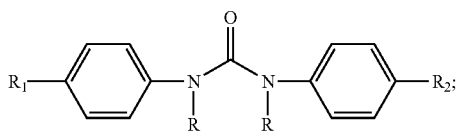

wherein in Formula (I) each $R_1$ and $R_2$ is independently:

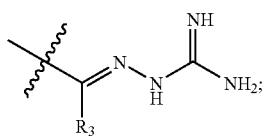

each $R_3$ is independently alkyl; and
each R is independently H or alkyl, wherein both R groups are not H;

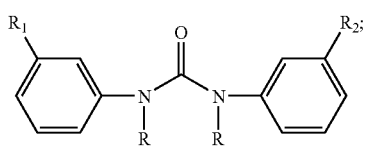

wherein in Formula II each $R_1$ and $R_2$ is independently:

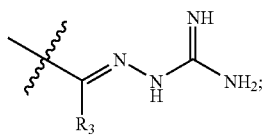

each $R_3$ is independently alkyl; and
each R is independently H or alkyl, wherein both R groups are not H;

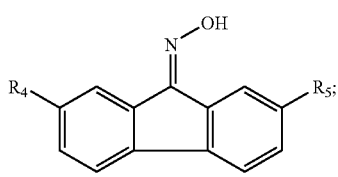

wherein each $R_4$ and $R_5$ is independently C(Me)=N(OH), $NO_2$, or H; wherein $R_4$ and $R_5$ are both not H.

Such pharmaceutical compositions may suitably comprise an additional therapeutic agent, such as an anticancer agent,

III. Methods of Treatment

In one embodiment, the present invention provides methods of treating disease and/or disorders or symptoms thereof which comprise administering a therapeutically effective amount of a pharmaceutical composition comprising a compound of the formulae herein to a subject (e.g., a mammal such as a human). Thus, one embodiment is a method of treating a subject suffering from or susceptible to a cancer or proliferative disease or disorder or symptom thereof. The method includes the step of administering to the mammal a therapeutic amount of an amount of a compound herein sufficient to treat the disease or disorder or symptom thereof, under conditions such that the disease or disorder is treated.

In one preferred aspect, methods for treating a subject suffering from or susceptible to a disease or disorder are provided, which methods may comprise (a) identifying the subject as in need of Chk2 inhibitor administration; and (b) administering to the subject one or more compounds as disclosed herein, including one or more compounds of any of Formulae (I) through (V) as those formulae are disclosed herein.

In another preferred aspect, methods for treating or preventing hypoxia, diabetes, strokes, or auto-immune disease in a subject are provided, which methods may comprise (a) identifying a subject as suffering from or susceptible to preventing hypoxia, diabetes, strokes, or auto-immune disease; and (b) administering to the subject one or more compounds as disclosed herein, including one or more compounds of any of Formulae (I) through (V) as those formulae are disclosed herein.

In yet another preferred aspect, methods for modulating Chk2 phosphorylation in a subject are provided, which methods may comprise (a) identifying a subject in need of modulated Chk2 phosphorylation; and (b) administering to the subject one or more compounds as disclosed herein, including one or more compounds of any of Formulae (I) through (V) as those formulae are disclosed herein. For instance, the Chk2 phosphorylation may be down regulation.

In a further preferred aspect, methods for protecting non-cancerous tissue in a subject are provided, which methods may comprise (a) identifying a subject in need protecting non-cancerous tissue; and (b) administering to the subject one or more compounds as disclosed herein, including one or more compounds of any of Formulae (I) through (V) as those formulae are disclosed herein.

In a still further preferred aspect, methods for reducing apoptosis in a non-cancerous cell (e.g. mammalian cells particularly human cells) of or in a subject are provided, which methods may comprise (a) identifying a subject in need of reducing apoptosis in non-cancerous cells; and (b) administering to the subject one or more compounds as disclosed herein, including one or more compounds of any of Formulae (I) through (V) as those formulae are disclosed herein.

In another preferred aspect, methods are provided for modulating a substrate in a normal cell (e.g. mammalian cells particularly human cells) of or in a subject, which methods may comprise (a) identifying a subject of such treatment; and (b) administering to the subject one or more compounds as disclosed herein, including one or more compounds of any of Formulae (I) through (V) as those formulae are disclosed herein.

In a further preferred aspect, methods are provided for method of sensitizing a cancer cell (e.g. mammalian cells particularly human cells) of or in a subject to one or more anticancer agents, which methods may comprise (a) identifying a subject in need of such treatment; and (b) administering to the subject one or more compounds one or more compounds as disclosed herein, including one or more compounds of any of Formulae (I) through (V) as those formulae are disclosed herein.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The preferred therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a cancer or proliferative disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The Chk2 inhibitor compounds herein may be also used in the treatment of any other disorders in which cell proliferation and migration may be implicated.

For therapeutic applications, the compounds of the formulae herein may be suitably administered to a subject such as a mammal, particularly a human, alone or as part of a pharmaceutical composition, comprising the formulae herein together with one or more acceptable carriers thereof and optionally other therapeutic ingredients. The carrier(s) must be "acceptable" in the sense of being compatible with the other ingredients of the formulation and not deleterious to the recipient thereof.

The pharmaceutical compositions of the invention include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets and sustained release capsules, and in liposomes, and may be prepared by any methods well known in the art of pharmacy. See, for example, Remington's Pharmaceutical Sciences, Mack Publishing Company, Philadelphia, Pa. (17th ed. 1985).

Such preparative methods include the step of bringing into association with the molecule to be administered ingredients such as the carrier which constitutes one or more accessory ingredients. In general, the compositions are prepared by uniformly and intimately bringing into association the active ingredients with liquid carriers, liposomes or finely divided solid carriers or both, and then if necessary shaping the product.

In certain preferred embodiments, the compound is administered orally. Compositions of the present invention suitable for oral administration may be presented as discrete units such as capsules, sachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion, or packed in liposomes and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface-active or dispersing agent. Molded tablets may be made by molding in a suitable machine a mixture of the powdered compound moistened with an inert liquid diluent. The tablets optionally may be coated or scored and may be formulated so as to provide slow or controlled release of the active ingredient therein. Methods of formulating such slow or controlled release compositions of pharmaceutically active ingredients, such as those herein and other compounds known in the art, are known in the art and described in several issued US patents, some of which include, but are not limited to, U.S. Pat. No. 4,369,172; and U.S. Pat. No. 4,842,866, and references cited therein. Coatings can be used for delivery of compounds to the intestine (see, e.g., U.S. Pat. Nos. 6,638,534, 5,217,720, and 6,569,457, and references cited therein).

A skilled artisan will recognize that in addition to tablets, other dosage forms can be formulated to provide slow or controlled release of the active ingredient. Such dosage forms include, but are not limited to, capsules, granulations and gel-caps.

Compositions suitable for topical administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access. Where an organ or tissue is accessible because of removal from the patient, such organ or tissue may be bathed in a medium containing the subject compositions, the subject compositions may be painted onto the organ, or may be applied in any convenient way.

As used herein, the terms "Chk2 inhibitor compound derivative" and "Chk2 inhibitor prodrug" are those based on Chk2 inhibitor compounds (including those of the formulae delineated herein) and include pharmaceutically acceptable derivatives or prodrugs thereof, respectively. A "pharmaceutically acceptable derivative or prodrug" means any pharmaceutically acceptable salt, ester, salt of an ester, or other derivative of a compound of this invention which, upon administration to a recipient, is capable of providing (directly or indirectly) an active compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or central nervous system) relative to the parent species. Preferred prodrugs include derivatives where a group which enhances aqueous solubility or active transport through the gut membrane is appended to the structure of formulae described herein. See, e.g., Alexander, J. et al. *Journal of Medicinal Chemistry* 1988, 31, 318-322; Bundgaard, H. *Design of Prodrugs*; Elsevier: Amsterdam, 1985; pp 1-92; Bundgaard, H.; Nielsen, N. M. *Journal of Medicinal Chemistry* 1987, 30, 451-454; Bundgaard, H. *A Textbook of Drug Design and Development*; Harwood Academic Publ.: Switzerland, 1991; pp 113-191; Digenis, G. A. et al. *Handbook of Experimental Pharmacology* 1975, 28, 86-112; Friis, G. J.; Bundgaard, H. *A Textbook of Drug Design and Development;* 2 ed.; Overseas Publ.: Amsterdam, 1996; pp 351-385; Pitman, I. H. *Medicinal Research Reviews* 1981, 1, 189-214.

The compounds of this invention may be modified by appending appropriate functionalities to enhance selective biological properties. Such modifications are known in the art and include those which increase biological penetration into a given biological compartment (e.g., central nervous system), increase oral availability, increase solubility to allow administration by injection, alter metabolism and alter rate of excretion. It will be appreciated that actual preferred amounts of a given compound herein used in a given therapy will vary according to the particular active compound being utilized, the particular compositions formulated, the mode of application, the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests, or by any method known in the art or disclosed herein.

The compounds herein may contain one or more asymmetric centers and thus occur as racemates and racemic mixtures, single enantiomers, individual diastereomers and diastereomeric mixtures. All such isomeric forms of these compounds are expressly included in the present invention. The compounds herein may also contain linkages (e.g., carbon-carbon bonds) wherein bond rotation is restricted about that particular linkage, e.g., restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. The term "N-oxides" refers to one or more nitrogen atoms, when present in an aromatic ring nitrogen-containing compound, that are in N-oxide oxidation form, i.e., N→O.

In certain method embodiments, a level of Marker or Marker activity in a subject is determined at least once. Comparison of Marker levels, e.g., to another measurement of Marker level obtained previously or subsequently from the same patient, another patient, or a normal subject, may be useful in determining whether therapy according to the invention is having the desired effect, and thereby permitting adjustment of dosage levels as appropriate. Determination of Marker levels may be performed using any suitable sampling/ expression assay method known in the art or described herein. Preferably, a tissue or fluid sample is first removed from a subject. Examples of suitable samples include blood, mouth or cheek cells, and hair samples containing roots. Other suitable samples would be known to the person skilled in the art.

Determination of protein levels and/or mRNA levels (e.g., Marker levels) in the sample can be performed using any suitable technique known in the art, including, but not limited to, enzyme immunoassay, ELISA, radiolabelling/assay techniques, blotting/chemiluminescence methods, real-time PCR, and the like.

Therefore, in certain embodiments, compounds of the invention, such as those of the formulae herein, are administered at dosage levels of about 0.0001 to 4.0 grams once per day (or multiple doses per day in divided doses) for adults. Thus, in certain embodiments of this invention, a compound herein is administered at a dosage of any dosage range in which the low end of the range is any amount between 0.1 mg/day and 400 mg/day and the upper end of the range is any amount between 1 mg/day and 4000 mg/day (e.g., 5 mg/day and 100 mg/day, 150 mg/day and 500 mg/day). In other embodiments, a compound herein, is administered at a dosage of any dosage range in which the low end of the range is any amount between 0.01 mg/kg/day and 90 mg/kg/day and the upper end of the range is any amount between 1 mg/kg/ day and 100 mg/kg/day (e.g., 0.5 mg/kg/day and 2 mg/kg/day, 5 mg/kg/day and 20 mg/kg/day, 50-150 mg/kg/day). The dosing interval can be adjusted according to the needs of individual patients. For longer intervals of administration, extended release or depot formulations can be used.

In one embodiment, the invention provides a method of monitoring treatment progress. The method includes the step of determining a level of diagnostic marker (Marker) (e.g., any target delineated herein modulated by a compound herein) or diagnostic measurement (e.g., screen, assay) in a subject suffering from or susceptible to a disorder or symptoms thereof associated with cancer, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

In other method embodiments, the levels of metabolites from the Chk2 inhibitor compounds can assessed. For example, the methods can further include assessment of levels of Chk2 inhibitors or Chk2 inhibitor derivatives (or metabolites thereof) resulting from the Chk2 inhibitors compounds or Chk2 inhibitor derivative compounds. Parameters such as the subject identification or selection for the treatment regimen, treatment efficacy, treatment protocol status or dosage range can be determined using these measurements.

IV. Kits

The invention also provides kits for treatment or prevention of a disease or disorder (or symptoms) thereof, including cancer, or a proliferative disease, disorder or symptom thereof. In one embodiment, the kit includes an effective amount of a compound herein in unit dosage form, together with instructions for administering the compound to a subject suffering from or susceptible to a disease or disorder or symptoms thereof. In other embodiments, the kit comprises a sterile container which contains the compound; such containers can be boxes, ampules, bottles, vials, tubes, bags, pouches, blister-packs, or other suitable container form known in the art. Such containers can be made of plastic, glass, laminated paper, metal foil, or other materials suitable for holding medicaments. The instructions will generally include information about the use of the compound of the formulae herein for treatment of a disease or disorder or symptoms thereof, including those of a disease or disorder (or symptoms) thereof of a proliferative nature. In other embodiments, the instructions include at least one of the following: description of the compound; dosage schedule and administration for treatment of a disease or disorder or symptoms thereof, including those of a proliferative nature; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The current application exploits new knowledge regarding selective CHK2 inhibitors. The prevention and treatment methods are contemplated to reduce apoptosis of normal (e.g., non-cancerous cells or tissue) or to sensitize cancerous cells or tissue to be more vulnerable to the compounds themselves or when co-administered with additional anticancer agents.

Combinations of substituents and variables envisioned by this invention are only those that result in the formation of stable compounds. The term "stable", as used herein, refers to compounds which possess stability sufficient to allow manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition that has been linked to Chk2 kinase modulation, or modulation of a metabolic pathway in which Chk2 kinase is involved).

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

The invention will be further described in the following examples. It should be understood that these examples are for illustrative purposes only and are not to be construed as limiting this invention in any manner.

EXAMPLES

Screening was performed at the Screening Technologies Branch at the National Cancer Institute (Frederick, Md.) using a high-throughput screening assay system capable of measuring Chk2 kinase activity. The assay is based on the IMAP assay developed by Molecular Devices. The assay is based on the high affinity binding of phosphate by immobilized metal (Mill) coordination complexes on nanoparticles and is depicted in FIG. 1. A fluorescein-labeled peptide substrate is used as the substrate for the kinase activity of Chk2 in the assay. The IMAP "binding reagent" stops the kinase reaction and complexes with phosphate groups on phosphopeptides generated in a kinase reaction, see FIG. 1. The binding of the "binding reagent" results in a change in the rate of the molecular motion of the peptide, and causes an increase in the fluorescence polarization value observed for the fluorescein label attached to the end of the peptide. Thus, inhibition of Chk2 in the assay would result in a decrease in fluorescence polarization compared to control.

Example 1

Figure 2:
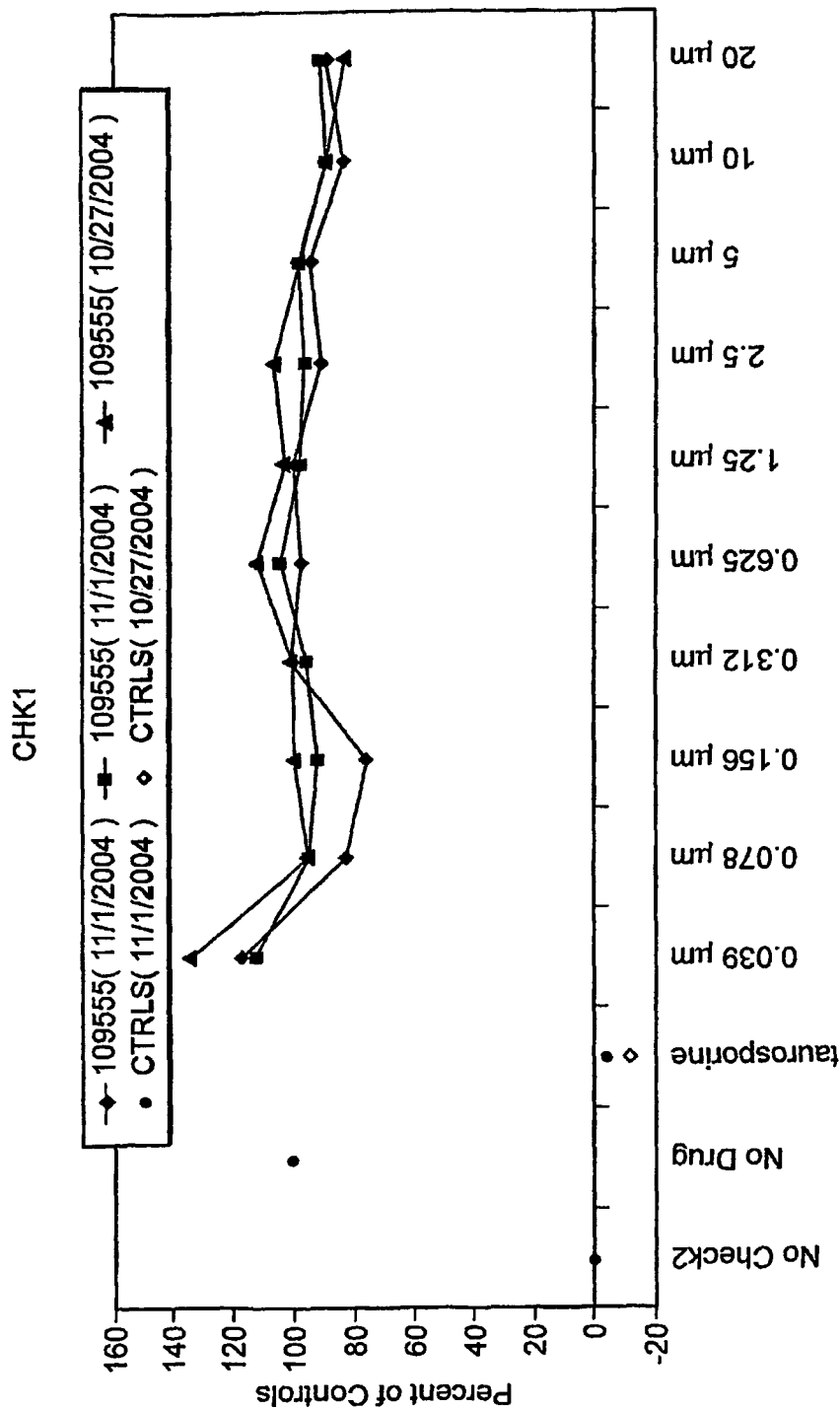
FIG. 2 illustrates effects of NSC 109555 on Chk1 activity. Three separate experiments are shown for NSC 109555. Staurosporine is shown as a positive control.
Figure 3:
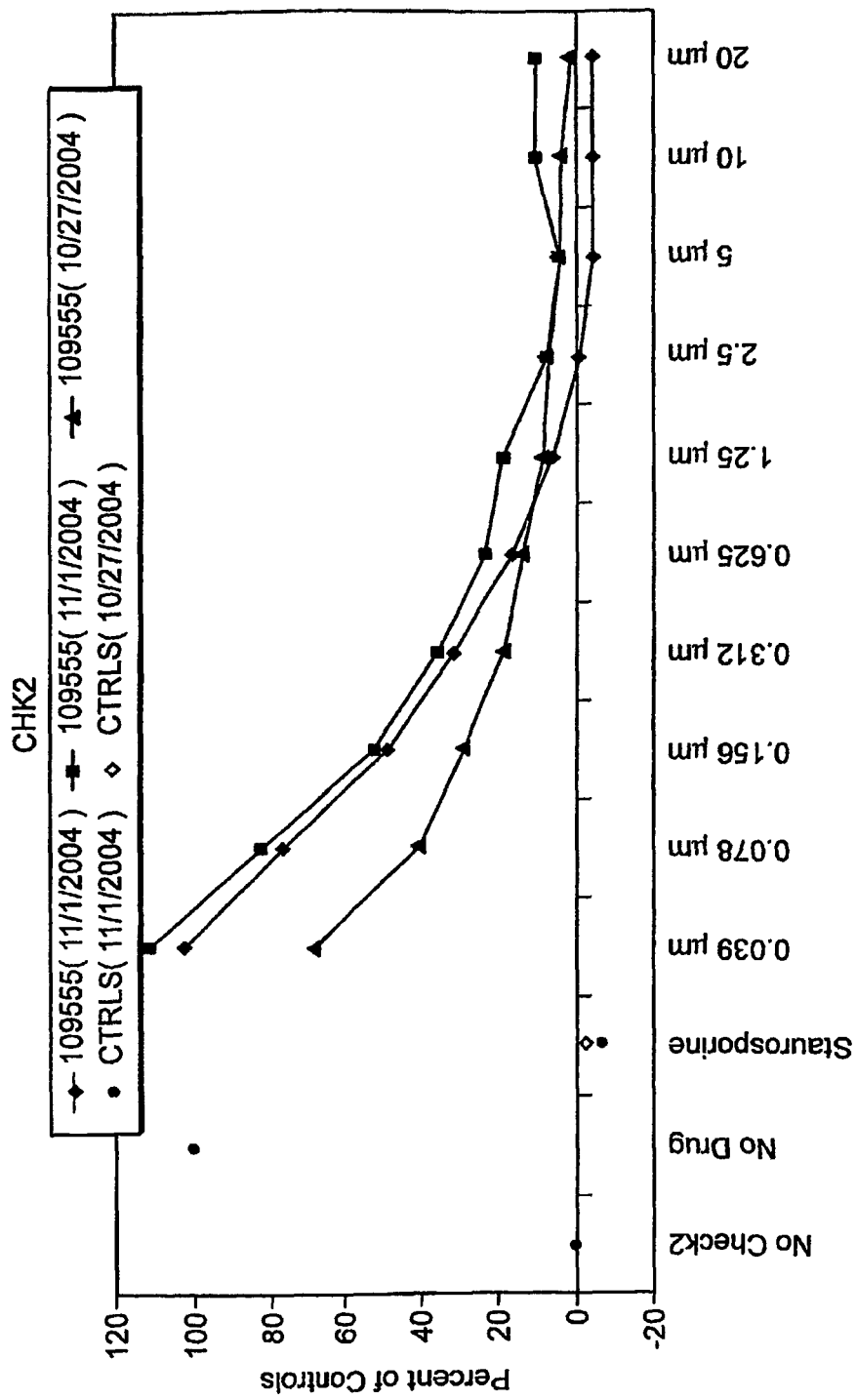
FIG. 3 illustrates effects of NSC 109555 on Chk2 activity. Three separate experiments are shown for NSC 109555. Staurosporine is shown as a positive control.

Compounds are screened for Chk2 inhibitory activity. Compounds identified as showing >50% Chk2 inhibition activity compared to inhibition by 5 µM staurosporine, are evaluated for their Chk1 inhibitory activity. Compound (I) [NSC 109555] is found to be specific for Chk2 and showed little or no inhibitory effect on Chk1 activity. See, FIGS. 2 and 3. The EC50 concentration is estimated to be 0.051 µM compared to an EC50 of 0.89 µM for the control compound, staurosporine. Compounds 5-8 show EC50s of ~4 µM; ~0.6-3.8 µM; ~0.8-4 µM; and ~20 µM; respectively.

Example 2

In Vitro Chk2 Kinase Assay

Following on from the data obtained from high-throughput screening, another assay is employed to measure Chk2 kinase activity. This assay is based on using $\gamma^{32}P$-labeled ATP to mediate phosphorylation of the target substrate and autophosphorylation of Chk2. Histone H1 or Cdc25C is used as test substrate. The reactions are performed at 30° C. for appropriate times, then the samples have 2×SDS loading buffer added to quench the reaction. The samples are boiled for about 5 minutes and then subjected to SDS-PAGE.

Figure 4:
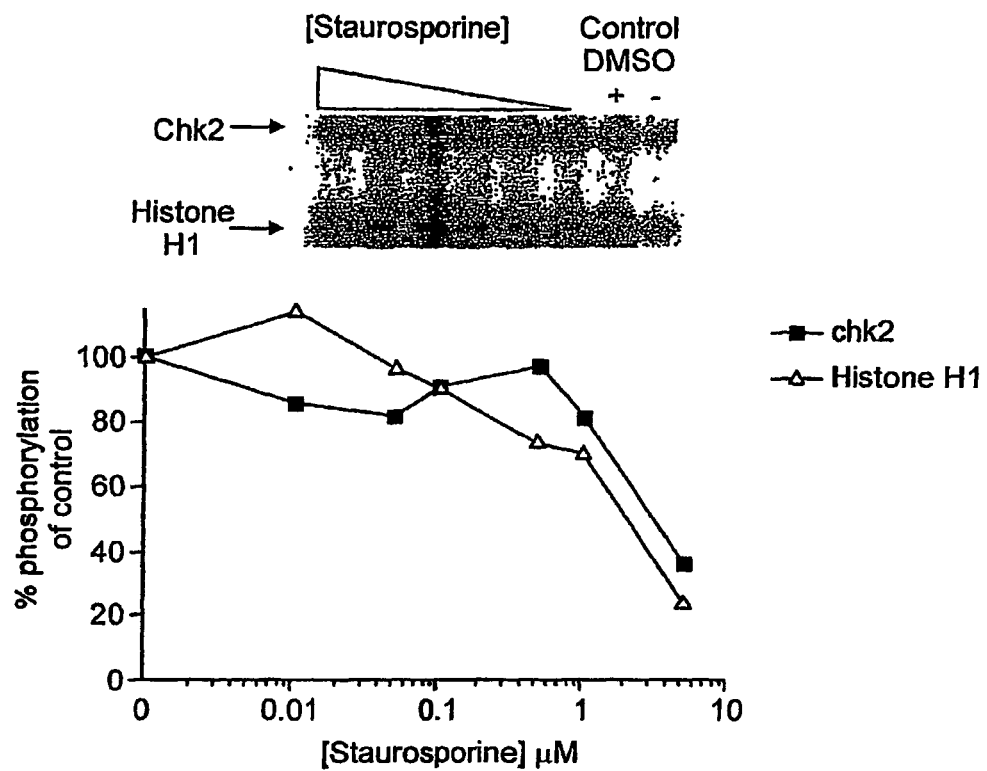
FIG. 4 illustrates inhibition of Chk2 kinase activity by staurosporine. Top bands indicate the level of Chk2 autophosphorylation, bottom bands indicate the level of histone H1 phosphorylation
Figure 5:
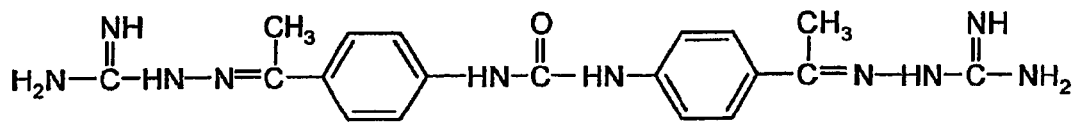
FIG. 5 illustrates inhibition of Chk2 kinase activity by NSC 109555 using an in vitro kinase assay. Top bands indicate the level of Chk2 autophosphorylation, bottom bands indicate the level of histone H1 phosphorylation.
Figure 5:
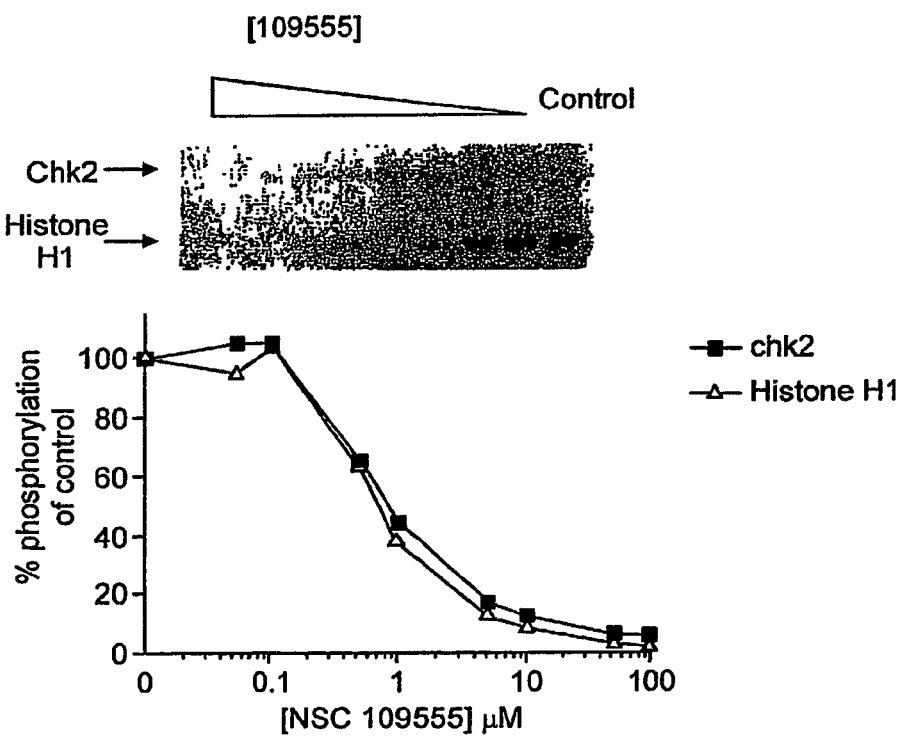
Figure 6:
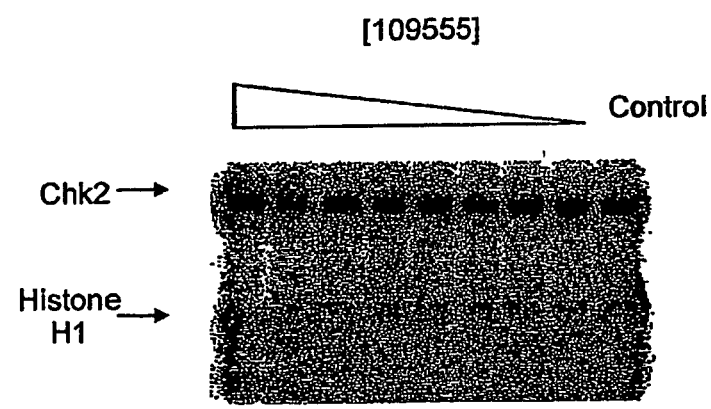
FIG. 6 illustrates inhibition of Chk1 kinase activity by NSC 109555 using an in vitro kinase assay. Top bands indicate the level of Chk1 autophosphorylation, bottom bands indicate the level of histone H1 phosphorylation.

Staurosporine is used as a positive control to confirm Chk2 inhibition (See, FIG. 4). Following on from this, NSC 109555 is used in this assay and is depicted in FIG. 5. It is clear that with increasing concentration of either staurosporine or NSC 109555, Chk2 kinase activity is inhibited. However, 109555, did not appear to inhibit the kinase activity of Chk1 (see, FIG. 6).

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

The recitation of a listing of chemical groups in any definition of a variable herein includes definitions of that variable as any single group or combination of listed groups. The recitation of an embodiment for herein includes that embodiment as any single embodiment or in combination with any other embodiments or portions thereof.

A number of embodiments of the invention have been described. Nevertheless, it will be understood that various modifications may be made without departing from the spirit and scope of the invention. Accordingly, other embodiments are within the scope of the following claims.

What is claimed:
1. A method of down regulating Chk2 phosphorylation in a subject, comprising:
(a) identifying the subject as suffering from lung cancer, breast cancer, bladder cancer, or melanoma; and
(b) administering to the subject an amount of one or more compounds of the following Formulae (I) or (II) sufficient to down regulate Chk2 phosphorylation:

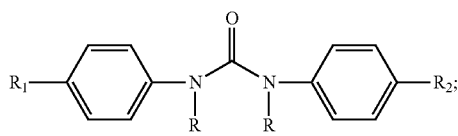

wherein each $R_1$ and $R_2$ is independently:

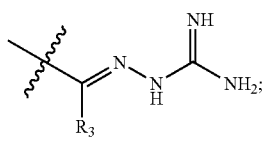

each $R_3$ is independently alkyl; and
each R is independently H or alkyl; or
a compound of Formula (II):

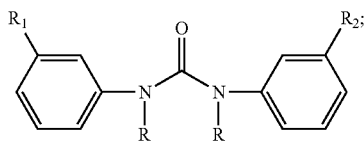

wherein each $R_1$ and $R_2$ is independently:

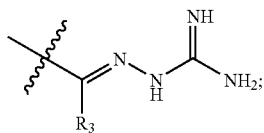

each $R_3$ is independently alkyl; and
each R is independently H or alkyl.

2. A method of protecting non-cancerous tissue in a subject suffering from lung cancer, breast cancer, bladder cancer, or melanoma, comprising:
(a) identifying the subject as having lung cancer, breast cancer, bladder cancer, or melanoma; and
(b) administering to the subject one or more compounds of the following Formulae (I) or

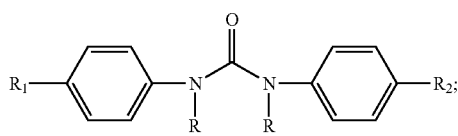

wherein each $R_1$ and $R_2$ is independently:

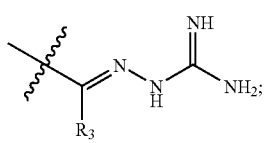

each $R_3$ is independently alkyl; and
each R is independently H or alkyl; or
a compound of Formula (II):

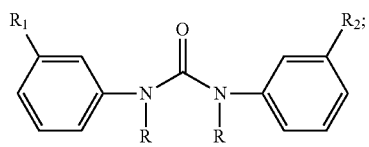

wherein each $R_1$ and $R_2$ is independently:

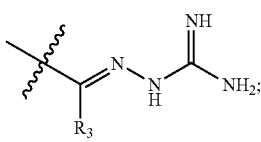

each $R_3$ is independently alkyl; and
each R is independently H or alkyl; and,
(c) administering ionizing radiation to the subject.

3. A method of inhibiting a substrate selected from p53, E2F1, and PML in a normal cell in a subject, comprising:
(a) identifying the subject of such treatment as suffering from lung cancer, breast cancer, bladder cancer, or melanoma; and
(b) administering to the subject an amount one or more compounds of the following Formulae (I) or (II) sufficient to inhibit p53, E2F1, or PML in the cell:

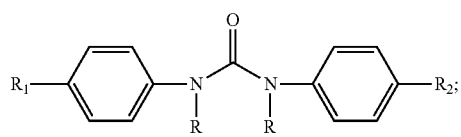

wherein each $R_1$ and $R_2$ is independently:
each $R_3$ is independently alkyl; and
each R is independently H or alkyl; or
a compound of Formula (II) sufficient to down regulate Chk2 phosphorylation:

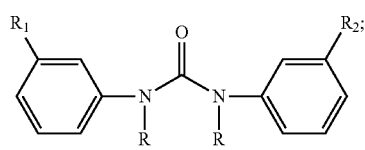

wherein each $R_1$ and $R_2$ is independently:

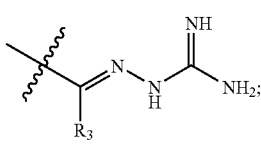

each $R_3$ is independently alkyl; and
each R is independently H or alkyl.

4. The method of claim 1, wherein the subject is a human.

5. The method of claim 1, further comprising administering an additional therapeutic agent.

6. The method of claim 1 wherein radiation is administered to the subject.

7. The method of claim 1 wherein the subject is suffering from melanoma.

8. The method of claim 1 wherein the subject is suffering from breast cancer.

9. The method of claim 5 wherein the additional agent is an anticancer agent, selected from topotecan, irinotecan, 9-amino camptothecin, or 9-nitro camptothecin.

10. The method of claim 2, wherein the subject is a human.

11. The method of claim 2, further comprising administering an additional therapeutic agent.

12. The method of claim 2 wherein the subject is suffering from melanoma.

13. The method of claim 2 wherein the subject is suffering from breast cancer.

14. The method of claim 11 wherein the additional agent is an anticancer agent, selected from topotecan, irinotecan, 9-amino camptothecin, or 9-nitro camptothecin.

15. The method of claim 3, wherein the subject is a human.

16. The method of claim 3, further comprising administering an additional therapeutic agent.

17. The method of claim 3 wherein radiation is administered to the subject.

18. The method of claim 3 wherein the subject is suffering from melanoma.

19. The method of claim 3 wherein the subject is suffering from breast cancer.

20. The method of claim 16 wherein the additional agent is an anticancer agent, selected from topotecan, irinotecan, 9-amino camptothecin, or 9-nitro camptothecin.

* * * * *